United States Patent [19]

McCallister

[11] 4,239,693

[45] Dec. 16, 1980

[54] PROCESS FOR PRODUCTION OF METHANOL

[75] Inventor: Robert A. McCallister, Mountain Lakes, N.J.

[73] Assignee: Foster Wheeler Energy Corporation, Livingston, N.J.

[21] Appl. No.: 51,325

[22] Filed: Jun. 22, 1979

[51] Int. Cl.³ .................. C07C 31/04; C07C 29/16
[52] U.S. Cl. ............................................. 260/449.5
[58] Field of Search ..................................... 260/449.5

[56] References Cited

U.S. PATENT DOCUMENTS

| | | | |
|---|---|---|---|
| 3,531,266 | 9/1970 | Chernoff | 260/449.5 |
| 3,598,527 | 8/1971 | Quartulli | 260/449.5 |
| 3,738,103 | 6/1973 | Rudolph et al. | 60/39.02 |
| 4,019,314 | 6/1977 | Springmann | 252/373 |
| 4,045,960 | 9/1977 | Cornelius et al. | 260/449.5 |
| 4,058,974 | 11/1977 | Pfenninger | 60/39.18B |

*Primary Examiner*—Howard T. Mars
*Attorney, Agent, or Firm*—Marvin A. Naigur; John E. Wilson; John J. Herguth, Jr.

[57] ABSTRACT

An improved process for the production of methanol is provided. A purge gas is removed from the synthesis reaction stage at an elevated pressure and is expanded prior to combustion in a gas turbine combustor. Exhaust gases are expanded and then sent to the reforming stage for either preheating reformer feed streams or providing heat necessary for the reforming of a feed stream with steam.

4 Claims, 2 Drawing Figures

PROCESS FOR PRODUCTION OF METHANOL

BACKGROUND OF THE INVENTION

This invention relates to an improvement in a process for the production of a crude reaction product such as liquid phase methanol. More specifically, this invention provides a method of utilizing purge gas commonly associated with the synthesis stage of the overall process so as to improve the efficiency of the overall process.

A typical methanol synthesis process includes reforming, energy recovery, compression and synthesis reaction stages. A purge gas is normally removed from the synthesis reaction stage and then used as a fuel in the reforming stage. According to the present invention, the purge gas is initially passed through an expander to provide mechanical energy, then used as a fuel for production of electrical energy and ultimately used as a souce of heat to generate steam, preheat feed streams, or heat reactants in the reforming stage. Since this method uses the potential energy associated with pressurized purge gas as well as the chemical energy of the purge gas, more efficient use of the total energy associated with the purge gas is achieved.

SUMMARY OF THE INVENTION

In accordance with an illustrative embodiment demonstrating features and advantages of the present invention there is provided an improvement in a process for the production of methanol which process includes reforming, energy recovery, compression and synthesis reaction stages.

A purge gas at an elevated pressure is removed from the synthesis reaction stage and is passed through an expander to recover energy from the purge gas line pressure. The expanded gas is combusted to yield a heated exhaust gas which is expanded and thereafter sent to the reforming stage.

BRIEF DESCRIPTION OF THE DRAWINGS

The above brief description as well as further objects, features and advantages of the present invention will be more fully appreciated by reference to the following description of presently preferred but nonetheless illustrative embodiments in accordance with the present invention when taken in connection with the accompanying drawings, wherein.

BRIEF DESCRIPTION OF THE PREFERRED EMBODIMENT

Figure 1:
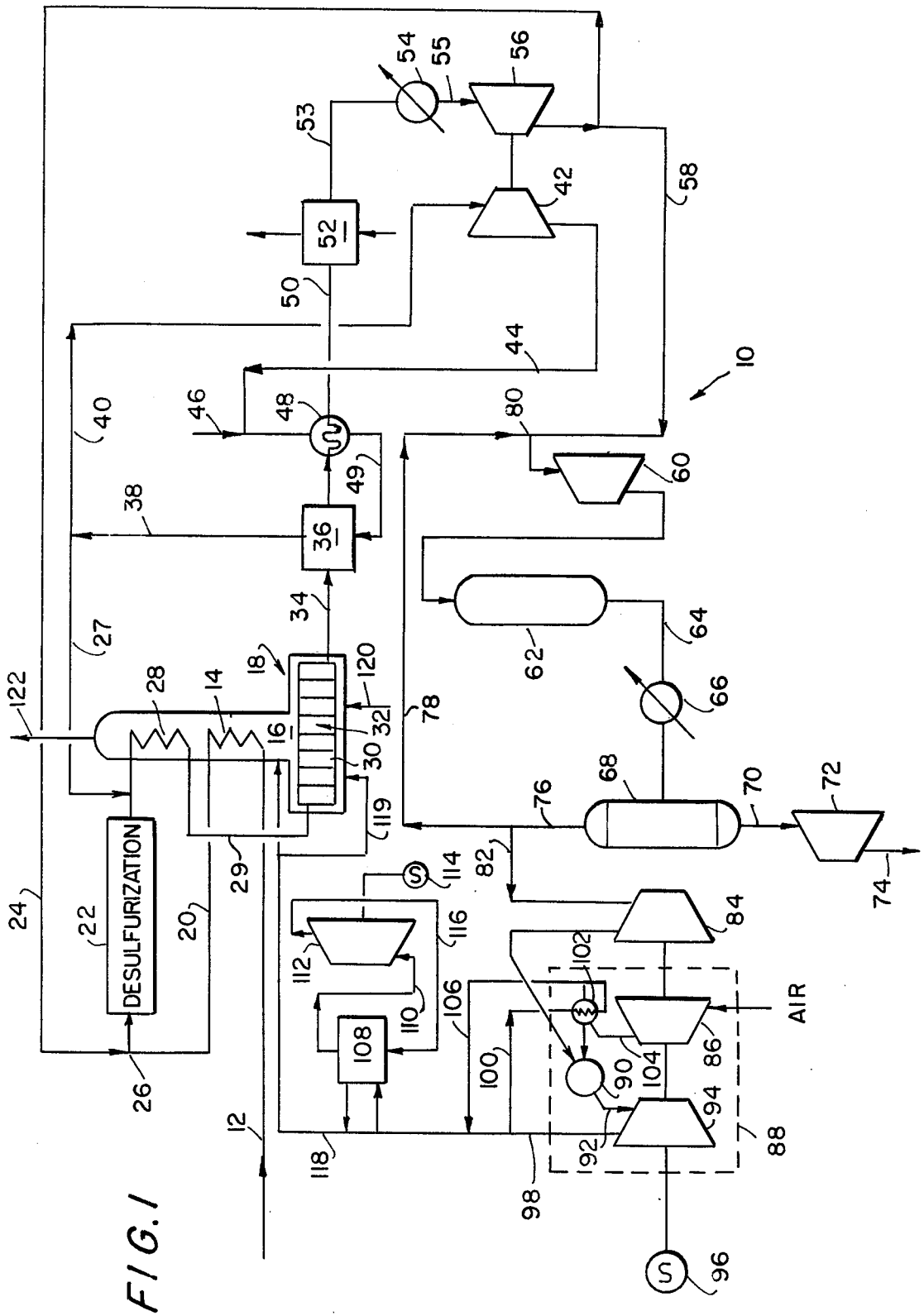
FIG. 1 is a schematic representation of a methanol synthesis process incorporating the present invention.

Referring to FIG. 1, there is shown a schematic diagram illustrative of a typical process 10 for production of methanol. In the preferred embodiment methanol is produced from natural gas. However, it is to be understood that other feedstocks such as naptha can be used, and other crude reaction products such as ammonia can be obtained.

A stream of natural gas is passed through line 12 into a preheater 14 disposed within the convection section 16 of primary reformer 18. Thereafter the preheated natural gas is passed through line 20 to desulfurizer 22. A stream of hydrogen gas is passed through line 24 and added to the preheated natural gas at a point 26 upstream of desulfurizer 22. The combined stream of natural gas and hydrogen is removed from desulfurizer 22, and added to a stream of steam flowing through line 27. The combined stream of natural gas, hydrogen, and steam is then passed into another preheater 28 disposed in convection section 16. The preheated combined stream is then passed via line 29 through a series of reformer tubes 30 filled with catalyst, such as a nickel-containing material, within the furnace section 32 of primary reformer 18. As the combination stream passes through the tubes 30 the natural gas, hydrogen and steam, react to yield a synthesis gas stream including carbon monoxide, carbon dioxide, and hydrogen gas. A portion of the natural gas usually does not react with a portion of the steam and therefore the gas stream obtained from the reforming stage will include carbon monoxide, carbon dioxide, hydrogen, steam and unreacted natural gas. This gas exits reformer 18 at a temperature of approximately 1500 degrees F. and is passed through line 34 into a waste heat boiler 36. In boiler 36 some of the heat is removed from the synthesis gas stream and is absorbed by water circulated through boiler 36, thereby generating steam which is removed from boiler 36 through line 38. A portion of the steam removed through line 38 is sent through line 27 for combination with the preheated natural gas and hydrogen stream. The remainder of the steam is passed through line 40 to an expander 42; after expansion the steam is sent through line 44, and supplemented by make-up water introduced through line 46. Thereafter the expanded steam and make-up water will pass through a feedwater heater 48 and then be recirculated to boiler 36 via line 49.

After passing through waste heat boiler 36 the synthesis gas is removed at a temperature of approximately 450 degrees F. and then passes through feedwater heater 48 wherein it gives off another portion of its heat to the boiler feedwater passing in an indirect heat exchange relation therethrough. Upon exiting heater 48 the temperature of the synthesis gas is approximately 425 degrees F. The synthesis gas is then passed via line 50 through a second waste heat boiler 52 for additional heat recovery. Although not shown, it is to be understood that this boiler could generate steam that would later be used for purification of the methanol. The synthesis gas is removed from the second waste heat boiler 52 at a temperature of approximately 340 degrees F. The synthesis gas is next sent via line 53 through a cooler 54 to further reduce the temperature of the synthesis gas to approximately 110 degrees F. It should be understood that a fan could also be used to cool the synthesis gas to this level, in which case the fan could be disposed upstream or downstream of cooler 54.

The synthesis gas removed from cooler 54 at approximately 110 degrees F. is at a pressure of approximately 400 psi. This gas is then sent via line 55 to compressor 56 in order to raise the pressure of the synthesis gas to approximately 1500 psi. Some hydrogen is bled from the gas stream at a point downstream of compressor 56, and is sent via line 24 to point 26 for addition to the feed stream. Thereafter the synthesis gas is passed through line 58 to a second stage of compression within compressor 60. The synthesis gas is compressed to approximately 1600 psi as it passes through compressor 60. The compressed synthesis gas is then introduced to reactor 62 wherein the carbon monoxide, carbon dioxide, and hydrogen gas react to form a product gas which includes methanol. The gaseous phase product is removed from reactor 62 through line 64 and then passed through partial condenser 66 wherein most of the methanol included in the product gas is condensed to a liquid phase. Thereafter the entire stream of product is introduced to separator drum 68. Within drum 68 the liquid methanol is separated from the gaseous portion of the crude reaction product and is removed through line 70. The liquid methanol is then compressed in liquid compressor 72 and is ultimately removed as crude liquid product through line 74. The gaseous portion of the crude reaction product is removed from drum 68 through line 76. A portion of the gaseous product is recirculated through line 78 and combined with incoming compressed synthesis gas at a point 80 upstream of compressor 60; the portion of the gaseous product passed through line 78 represents approximately 90% of the gaseous product removed from drum 68, and is commonly referred to as "recycle" gas. The remaining portion of the gaseous product removed from drum 68 is passed through line 82; this portion of the gaseous product is commonly referred to as "purge" gas. The purge gas comprises hydrogen, carbon monoxide, carbon dioxide, steam, gaseous methanol, and unreacted natural gas. Normally the purge gas is sent to the furnace section of primary reformer 18, and is combusted as a fuel to provide heat necessary to promote the reaction of the natural gas with steam within reformer tubes 30.

According to the present invention the purge gas is sent through a line 82 to an expander 84 wherein the purge gas is expanded from a pressure of approximately 1400 psi to a pressure of approximately 210 psi. Expander 84 drives one or more compressor services, such as compressor 86 associated with gas turbine 88. The expanded purge gas is then sent to the gas turbine combuster 90 wherein it is burned with an oxygen-containing gas such as air. A heated exhaust gas is removed from gas turbine combustor 90 through line 92 and is expanded in gas turbine expander 94 which drives electrogenerator 96, thereby producing electrical energy. Expanded exhaust gas is removed from expander 94 through line 98. Some or all of the exhaust gases can be sent through line 100 into preheater 102. Within preheater 102 the exhaust gases come in indirect heat exchange contact with the air charge which has been compressed in compressor 86, and sent through line 104 to combustor 90, thereby preheating the air charge before its introduction to the combustor. The exhaust gases are then routed through line 106 back into line 98 where they combine with the remainder of the exhaust gases passing through line 98.

The exhaust gases can thereafter be sent directly to the primary reformer, or all or a portion of the gases can first be passed through a waste heat boiler 108. When the boiler 108 is used, the exhaust gases give up some of their heat to generate steam within boiler 108; the steam is removed through line 110 and then used to drive a steam expander 112. Steam expander 112 drives an electrogenerator 114 which generates electrical energy. The expanded steam is then recirculated through line 116 back into boiler 108. The exhaust gases, if not passed through waste heat boiler 108, or after being passed through boiler 108 are then routed through line 118 to the reforming stage of the overall methanol process. A branch line 119 connects between line 118 and the furnace section of primary reformer 18. Since the exhaust gases are rich in oxygen, all or a portion of the exhaust gas can be used as a source of preheated oxygen for use in the furnace section of reformer 18 for combustion therein with a fuel introduced through line 120. The remaining portion of the exhaust gases flowing through line 118 are introduced into the convection section 16 of reformer 18 in order that they may give up additional heat to the streams flowing through preheaters 14, 28. The exhaust gas is ultimately removed from reformer 18 through line 122.

Figure 2:
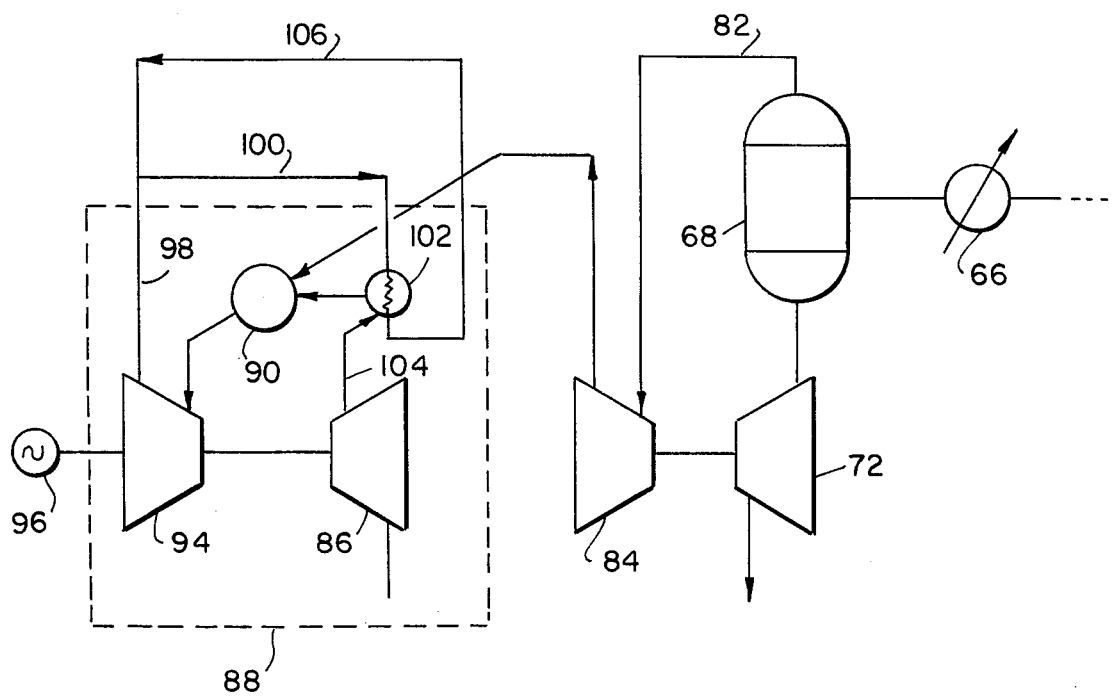
FIG. 2 is a schematic representation of an alternative arrangement of the present invention.

Referring to FIG. 2, an alternative embodiment of the invention is shown, wherein expander 84 drives liquid compressor 72 rather than compressor 86. It is to be understood that the expander 84 can be used to drive other compressor services, bearing in mind that the principal aspect of the invention relates to the use of the potential energy of the pressurized purge gas as well as its chemical energy so as to improve the efficiency of the overall process.

In order to illustrate the advantages of the present invention, the following example is provided:

EXAMPLE

In this example the purge gas is removed from drum 68 at a pressure of approximately 1400 psig, passed through line 82 to expander 84 wherein it is reduced to a pressure of approximately 210 psig. In the case of a 500 MT/day methanol plant, the purge gas has a net heating value of approximately 310 BTU per standard cu. ft. This gas may be burned in gas turbine 88 to produce approximately 40 megawatts of electricity at electrogenerator 96 after expansion through expander 94. The gas turbine exhaust will be removed through line 98 at a temperature of approximately 1000 degrees F. When the exhaust is used to heat water in boiler 108, additional electrical energy can be generated at electrogenerator 114.

Since gas turbines are usually supplied with excess air in order to keep the temperature of the exhaust gases below an acceptable upper limit imposed by materials from which gas turbine components are made (approximately 2000 degrees F.) the exhaust gas is rich in oxygen. This oxygen rich preheated stream can be introduced through line 119 to the furnace section 32 for combustion with a fuel provided via line 120, or can be passed into convection section 16 for heating feed streams passing through preheaters 14, 28.

A latitude of modification, change and substitution is intended in the foregoing disclosure and in some instances some features of the invention will be employed without a corresponding use of other features. Accordingly, it is appropriate that the appended claims be construed broadly and in a manner consistent with the spirit and scope of the invention herein.

What is claimed is:

1. In a process for the production of methanol including reforming, energy recovery, compression and synthesis reaction stages, wherein a purged gas at an elevated pressure is removed from said synthesis reaction stage, the improvement comprising the steps of
   (a) passing said purged gas through an expander, said expander being operatively connected to a compressor, so as to recover energy from said purged gasline pressure and to use said energy to drive said compressor,
   (b) combusting said expanded purged gas with an oxygen-containing gas to obtain a heated exhaust gas, said heated exhaust gas including oxygen, (c) expanding said heated exhaust gas to recover energy therefrom, and (d) passing said expanded heated exhaust gas to said reformed stage, a portion of said heated exhaust gas containing oxygen being combusted with a fuel in said reforming stage to generate heat for use in said reforming stage.

2. The improvement of claim 1 further comprising the step of passing a portion of said expanded heated exhaust gas through an indirect heat exchanger for preheating said oxygen containing gas prior to combustion of said oxygen containing gas with said purge gas.

3. The improvement of claim 1 further comprising the step of passing said expanded heated exhaust gas through a waste heat boiler prior to the passage of said gas to said reforming stage.

4. The improvement of claim 1 wherein said step of passing said expanded heated exhaust gases to said reforming stage comprises passing one portion of said gases through a reformer convection section for preheating reforming stage feed streams, and passing the remainder of said gases into a reformer furnace section for combustion of said portion of oxygen contained in said gas.

* * * * *